US009714896B2

(12) United States Patent
Horvath Szabo et al.

(10) Patent No.: US 9,714,896 B2
(45) Date of Patent: Jul. 25, 2017

(54) SYSTEM AND METHODOLOGY FOR DETERMINING PROPERTIES OF A SUBSTANCE

(71) Applicant: Schlumberger Technology Corporation, Sugar Land, TX (US)

(72) Inventors: Gaza Horvath Szabo, Alberta (CA); Sharath Chandra Mahavadi, Alberta (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 99 days.

(21) Appl. No.: 14/762,491

(22) PCT Filed: Feb. 17, 2014

(86) PCT No.: PCT/US2014/016691
§ 371 (c)(1),
(2) Date: Jul. 22, 2015

(87) PCT Pub. No.: WO2014/158436
PCT Pub. Date: Oct. 2, 2014

(65) Prior Publication Data
US 2015/0355068 A1 Dec. 10, 2015

Related U.S. Application Data

(60) Provisional application No. 61/804,730, filed on Mar. 24, 2013.

(51) Int. Cl.
*G01F 1/88* (2006.01)
*G01N 15/08* (2006.01)
(Continued)

(52) U.S. Cl.
CPC ............... *G01N 15/08* (2013.01); *G01F 1/88* (2013.01); *G01N 15/0826* (2013.01); *G01N 33/2823* (2013.01)

(58) Field of Classification Search
CPC ...... G01F 1/88; G01N 15/08; G01N 15/0826; G01N 13/00; G01N 33/2823; G01N 11/00; G01N 11/04; G01N 11/08
See application file for complete search history.

(56) References Cited

U.S. PATENT DOCUMENTS 4,586,376 A * 5/1986 Outmans ................. E21B 49/00
73/38
4,907,448 A * 3/1990 Givens ................. G01N 33/241
324/376
(Continued)

OTHER PUBLICATIONS

Pang, Zhan-Xi, "The Blocking Ability and Flowing Characteristics of Steady Foams in Porous Media", Transp. Porous. Med. (2010) Vo. 85, pp. 299-316.
(Continued)

*Primary Examiner* — Nguyen Ha
(74) *Attorney, Agent, or Firm* — Bridget M. Laffey

(57) ABSTRACT

A methodology and system determine properties of a sample substance, such as a liquid/foam used to control sweep homogeneity problems in an earth formation. The methodology and system utilize a core of formation simulation material placed in a container. An injection system is coupled to the container and enables placement of both the sample substance and an injection fluid into the container. The injection fluid is injected under pressure and moves the sample substance through the core. A data acquisition system is employed to measure parameters such as pressure differentials along the core as the sample substance propagates through the formation simulation material. The pressure differentials may be evaluated over time by the data
(Continued)

acquisition system to determine fluid breakthrough properties of the sample substance.

13 Claims, 4 Drawing Sheets

(51) Int. Cl.
    *G01N 13/00*     (2006.01)
    *G01N 11/00*     (2006.01)
    *G01N 11/04*     (2006.01)
    *G01N 11/08*     (2006.01)
    *G01N 33/28*     (2006.01)

(56) References Cited

U.S. PATENT DOCUMENTS

| | | |
|---|---|---|
| 5,129,457 A | 7/1992 | Sydansk |
| 5,463,805 A | 11/1995 | Mowry et al. |
| 6,325,147 B1 | 12/2001 | Doerler et al. |
| 2006/0157282 A1 | 7/2006 | Tilton et al. |
| 2007/0062258 A1* | 3/2007 | Egermann ............ E21B 41/0064 73/38 |
| 2011/0192598 A1 | 8/2011 | Roddy et al. |

OTHER PUBLICATIONS

International Search Report and Written Opinion for corresponding PCT Application No. PCT/US2014/016691, dated Jul. 14, 2014, 12 pages.

* cited by examiner

SYSTEM AND METHODOLOGY FOR DETERMINING PROPERTIES OF A SUBSTANCE

BACKGROUND

The development of enhanced oil recovery processes, including water, chemical, and steam flooding; steam and carbon dioxide injection; and in situ combustion has allowed the recovery of greater percentages of original oil-in-place. The effectiveness of these processes tends to be restricted by sweep homogeneity problems, such as gravity override, fingering, and channeling. In each case, fluid, e.g. gas, preferentially sweeps highly permeable portions of the reservoir leaving a substantial amount of the original oil-in-place. A technology used to mitigate the sweep homogeneity problems employs injection of mobility controlling foams stabilized by surfactants or colloidal particles to limit the fluid, e.g. gas, breakthrough. The characteristics of the mobility controlling foam can be difficult to predict for actual downhole, well-related applications.

SUMMARY

In general, the present disclosure provides a methodology and system for determining properties of a sample substance, such as a liquid/foam used to control sweep homogeneity problems in an earth formation. The technique comprises placing a core of formation simulation material, e.g. sand, in an injection container. An injection system is coupled to the injection container and used to place both the sample substance and an injection fluid into the injection container. The injection fluid is injected under pressure and moves the sample substance through the core. A data acquisition system is employed to measure parameters, such as pressure differentials along the core, as the sample substance propagates through the formation simulation material. In some applications, the pressure differentials are evaluated over time by the data acquisition system to determine fluid breakthrough properties of the sample substance, while in other applications the flow rates are evaluated over time by the data acquisition system to determine fluid breakthrough properties of the sample substance.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate various implementations described herein and are not meant to limit the scope of various technologies described herein, and.

DETAILED DESCRIPTION

Figure 1:
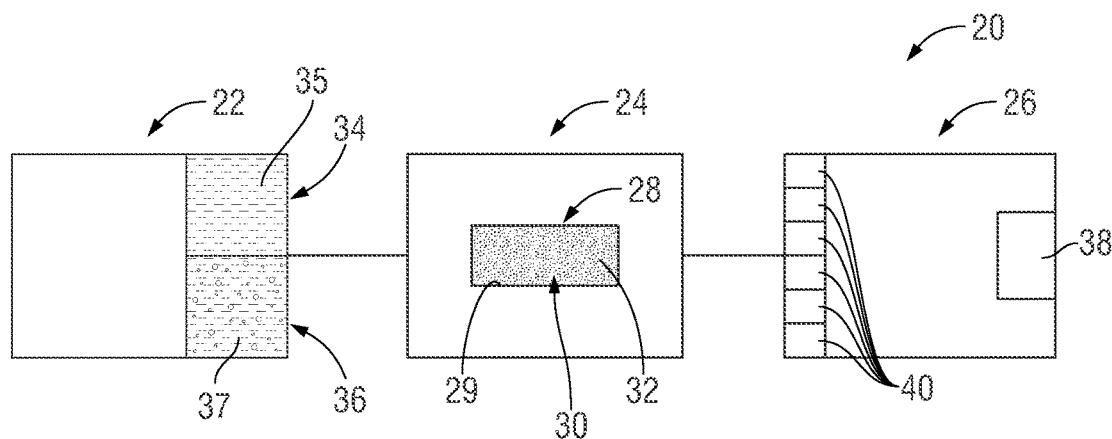
FIG. 1 is a schematic representation of an example of a system for determining properties of a sample substance, according to an embodiment of the disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a system and methodology for determining properties of a sample substance, e.g. a liquid/foam used to control sweep homogeneity problems in an earth formation. By way of example, the sample substance may be a sample of a foaming liquid employed to increase the effectiveness of enhanced oil recovery processes by limiting gas breakthrough. The amount of oil recovery from a given formation can be substantially increased by utilizing these types of liquids to reduce sweep homogeneity problems.

The present technique facilitates testing the effectiveness of various foaming liquids and other substances. An embodiment of the technique comprises placing a core of formation simulation material, e.g. sand or rock, in an injection container. An injection system is coupled to the injection container and used to inject both the sample substance and an injection fluid into the injection container. The injection fluid, e.g. nitrogen gas, is injected under pressure and moves the sample substance through the core. A data acquisition system is employed to measure parameters such as pressure differentials along the core as the sample substance propagates through the formation simulation material. The pressure differentials and sample substance propagation can be used to determine the effectiveness of such a substance when used in a specific formation formed of a material comparable to the formation simulation material. In some applications, for example, the pressure differentials may be evaluated over time by the data acquisition system to determine fluid breakthrough properties of the sample substance. The fluid breakthrough properties may provide indications of sweep homogeneity problems, such as gravity override, fingering, and channeling.

Foams may be applied as selective mobility controlling and flow profile-modifying agents to substitute low viscosity sweeping fluids in the reservoir or other porous media. With various types of liquid substances, foams are generated in the porous media, e.g. formation, when gas and surfactant solution are injected either simultaneously or intermittently. During this injection process, foams are formed with the dispersion of non-wetting gases such as steam, carbon dioxide, and/or nitrogen in the wetting liquid phase which contains surfactant. By way of example, aqueous surfactant foams may be used to improve carbon dioxide flood performance, to improve steam drive, to prevent or delay gas/water coning, to plug high permeability channels via gelled foams, and/or to clean up groundwater aquifers with surfactant-alternating gas processes. In various formations and other types of porous media, the propagation of foams is closely related to the geometry and conductivity of the pores within the media.

Foams also may be used to reduce gas mobility and to delay the gas breakthrough time in parallel wells. The effect of foams on the alteration of gas breakthrough time is related to foam properties. Consequently, the gas breakthrough time can be used to characterize foam properties. The ability of foams to delay gas breakthrough is as effective as the ability of foams to divert sweeping fluid from high permeability to low permeability regions. Embodiments described herein facilitate accurate testing of gas breakthrough time for a variety of sample substances, such as foaming sample substances. However, other types of foams and substances also may be tested by the systems and methodologies described herein.

Referring generally to FIG. 1, a schematic representation is provided to illustrate a system for testing and studying the blocking ability of substances, e.g. foams, at reservoir conditions. The system may be used as an apparatus for determining gas breakthrough times and is designed to screen the aqueous solutions of chemicals for their ability to delay gas breakthrough. In some applications, the system also may be used to determine other substance characteristics, e.g. rheological behavior of foam in porous media. The testing and analysis enables selection of a suitable chemical for enhanced oil recovery in a given formation.

In the embodiment of FIG. 1, a system 20 for determining properties of a sample substance is illustrated. In this example, system 20 comprises an injection system 22, an injection container system 24, and a data acquisition and analysis system 26. The injection container system 24 comprises a container 28 having an injection chamber 29 filled with a core 30 of formation simulation material 32. By way of example, formation simulation material 32 may comprise sand and/or a variety of other types of porous media representative of formation properties for a given reservoir or reservoirs.

The illustrated injection system 22 is coupled to the injection container system 24 and comprises a sample injector 34 positioned to inject a sample substance 35 into injection chamber 29 and formation simulation material 32. The injection system 22 also comprises a fluid injector 36, such as a gas injector. The fluid injector 36 may be used to inject a gas 37 or other suitable fluid into container 28 after the sample substance 35 (e.g. a foaming sample substance) penetrates into the formation simulation material 32 under pressure to cause propagation of the foam sample or other substance.

The illustrated data acquisition and analysis system 26 also is coupled to the injection container system 24. In some embodiments, data acquisition and analysis system 26 may comprise a processor 38 in communication with a plurality of sensors 40, such as pressure sensors and temperature sensors. In some embodiments, a plurality of pressure sensors 40 may be deployed along the container 28. The pressure sensors 40 provide data to the processor 38 for determination of pressure differentials along the core 30 of formation simulation material 32. Under constant injection rate conditions the change in pressure differentials over time provides an indication of gas breakthrough within the core 30, and this gas breakthrough information is used to determine characteristics of the sample substance, e.g. foam sample. Under constant differential pressure conditions between the entry and exit points of the container 28 the change in flow rate over time provides an indication of gas breakthrough within the core 30, and this gas breakthrough information is used to determine characteristics of the sample substance, e.g. foam sample.

Figure 2:
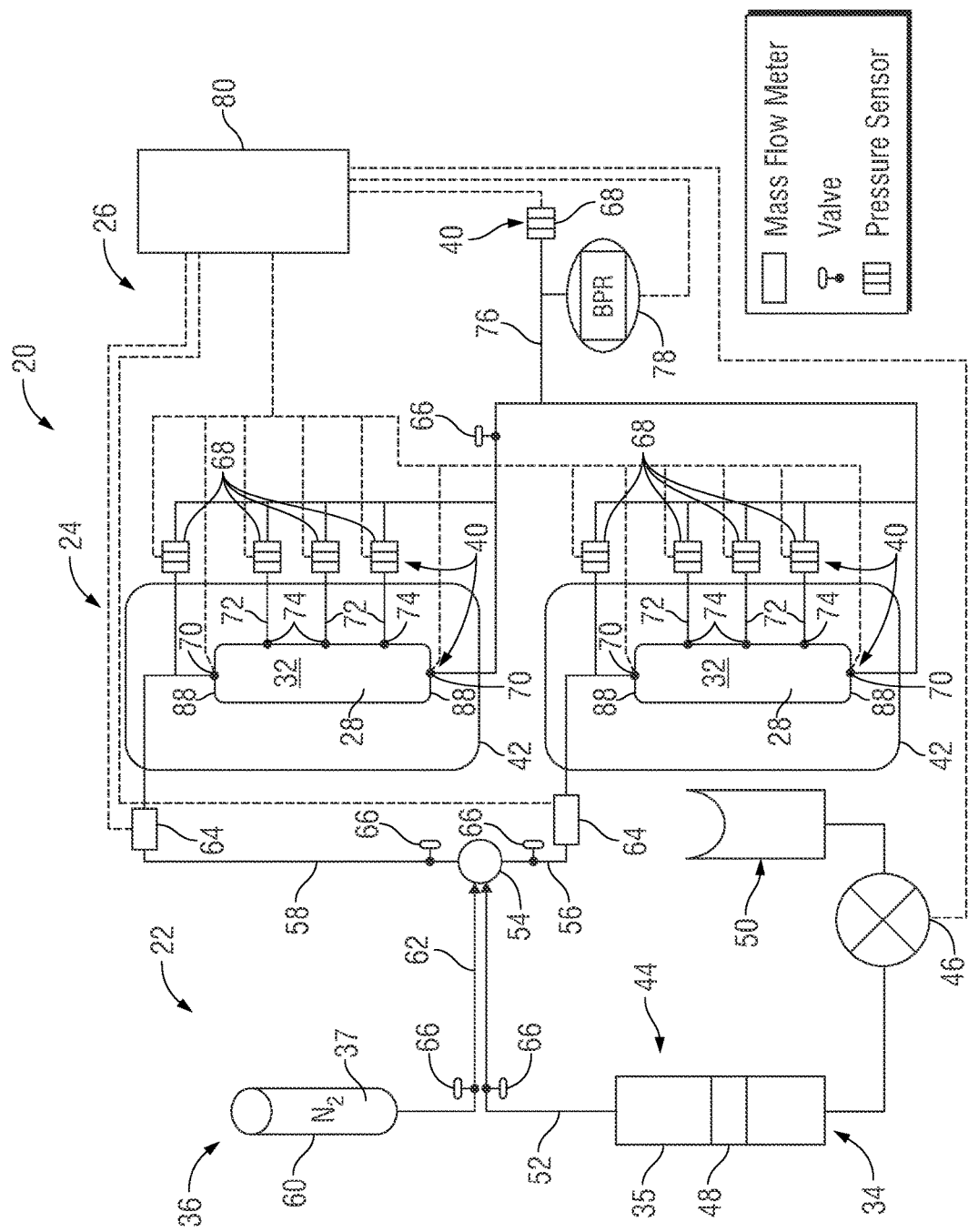
FIG. 2 is a schematic illustration of a more detailed example of a system for determining properties of a sample substance, when the methodology of FIG. 5 is utilized, according to an embodiment of the disclosure.

Referring generally to FIG. 2, a more detailed example of an embodiment of a system 20 for determining properties of a sample substance is illustrated. In this example, the injection container system 24 comprises a plurality of injection containers 28, e.g. a pair of injection containers 28, in the form of injection cylinders. Each container 28 is filled with core 30 of appropriate formation simulation material 32 and is placed in a controlled heating bath 42, such as a controlled heating air bath. The controlled heating bath 42 encloses the core 30 of formation simulation material 32, e.g. a sand pack. In some embodiments, the controlled heating bath 42 or another suitable heating bath may be designed to enclose injection system 22 so as to enable heating of the formation simulation material 32, the sample substance 35, and/or the injection fluid/gas 37. By way of example, the controlled heating bath 42 may be designed to heat the various materials to a suitable wellbore temperature.

In the example illustrated, the sample injector 34 of injection system 22 comprises a sample bottle 44 which contains sample substance 35. Sample bottle 44 is coupled to a high precision pump 46 which is controlled to pump a fluid to sample bottle 44. The fluid pumped via pump 46 moves a piston 48 within sample bottle 44 to inject the sample substance into containers 28 and formation simulation material 32. The high precision pump 46 receives pump fluid from a reservoir 50. When the pump 46 is activated to move piston 48, the sample substance 35 is forced from sample bottle 44 and moves along a fluid flow line 52 to a junction 54 where the sample substance 35 (fluid sample 35) is split for flow to each container 28 via fluid flow lines 56 and 58, respectively.

The illustrated injection system 22 also comprises fluid injector 36 in the form of, for example, a pressurized gas bottle 60. By way of example, the pressurized gas bottle 60 may contain nitrogen 37, such as a non-condensable nitrogen. The pressurized gas bottle 60 is designed to inject the injection fluid 37 into containers 28 via a fluid flow line 62 coupled with junction 54. From junction 54, the injection fluid 37, e.g. nitrogen, is injected along fluid flow lines 56 and 58, respectively, until forced under pressure into the formation simulation material 32 within each container 28. The injection system 22 also may comprise a mass flow meter 64 associated with each container 28 and a plurality of valves 66 disposed along fluid flow lines 52, 56, 58 and 62. The mass flow meters 64 are designed to detect the flow rate of the injected fluid, e.g. nitrogen, when the system 20 is operated as described in FIG. 5 (i.e. the formation simulation material 32 is first saturated with the sample substance 35 by operating pump 46. Then valve 66 in fluid flow line 52 is closed and the fluid, e.g. gas 37, is injected under constant differential pressure condition through the formation simulation materials 32 situated in the containers 28, while the mass flow meters 64 monitor the flow rates of the injected fluid 37 as a function of time. Such mass flow meters (available from Bronkhorst USA Inc. of Bethlehem, Pa., USA) are able to measure the gas flow rate in the range of 0.1 to 5.0 liters per minute at 3000 psi (210.9 kg/square cm), for example.

The illustrated system 20 further comprises data acquisition and analysis system 26 which comprises sensors 40 associated with each injection container 28 and corresponding core 30. By way of example, the sensors 40 may comprise a plurality of pressure sensors 68, e.g. pressure transducers, and temperature sensors 70, e.g. thermocouples. A portion of the pressure sensors 68 may be positioned along each core 30 to measure pressure differentials and changes in the pressure differentials along each core 30. In some applications, the pressure sensors 68 are pressure gauges coupled with each injection container 28 via fluid lines 72 engaging taps/ports 74 extending through a sidewall of each container 28. The various fluid lines 72 may be joined with a common pressure/flow line 76 and a back pressure regulator 78. An additional pressure sensor 68 may be positioned adjacent the back pressure regulator 78, as illustrated. In this example, the temperature sensors 70 may be located at the ends of the cores 30 of formation simulation material 32.

As illustrated, the various sensors 40, e.g. pressure sensor 68 and temperature sensors 70, may be coupled with a data processing unit 80. The mass flow meters 64 also may be connected with data processing unit 80. Depending on the specifics of a given application, the data processing unit 80 may be a single unit or multiple units having data processing and/or control capability. For example, the data processing unit 80 may comprise a processor programmed to process the various pressure and temperature data in a manner which provides data on gas breakthrough or other parameters related to the sample substance 35 being tested.

Figure 3:
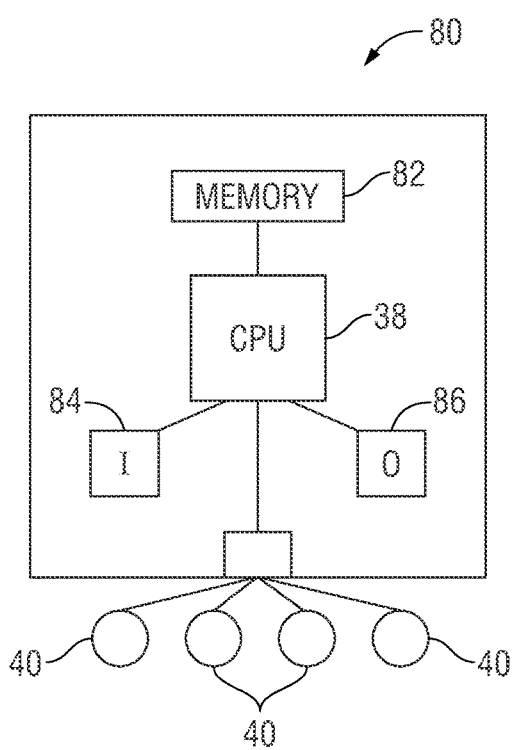
FIG. 3 is a schematic illustration of a processing system which may be used to process data obtained from sensors of a data acquisition system employed in the system for determining properties of a sample substance, according to an embodiment of the disclosure.

Referring also to FIG. 3, an example of data processing unit 80 is illustrated. In this particular example, the various data collected by sensors 40 may be output to and processed on data processing unit 80. In some applications, data processing unit 80 may be in the form of a computer-based processing system in which computers are programmed to process the sensor data. Based on the changing pressure differentials, for example, the data can be used to determine gas breakthrough times for various foam samples or other types of substance samples.

If data processing unit 80 is in the form of a computer-based system, the system may comprise processor 38 in the form of a central processing unit (CPU). The processor 38 is operatively employed to intake and process data obtained from the sensors 40. The processor 38 also may be operatively coupled with a memory 82, an input device 84, and an output device 86. Input device 84 may comprise a variety of devices, such as a keyboard, mouse, voice recognition unit, touchscreen, other input devices, or combinations of such devices. Output device 86 may comprise a visual and/or audio output device, such as a computer display, monitor, or other display medium having a graphical user interface. Additionally, the processing may be done on a single device or multiple devices locally, at a remote location, or with some local devices and other devices located remotely. The various analyses, sample parameters collected, modeling results, and/or other types of processed data may be stored in memory 82 and evaluated to determine the effectiveness of a given foam or other material in facilitating enhanced oil recovery.

Referring again to FIG. 2, the containers 28 are illustrated as injection cylinders placed in vertical positions. This vertical positioning of the containers 28 mitigates gas breakthrough due to gravity segregation during the experiments, as gas rather than foams is injected in certain measurements. However, other configurations can be used depending on the goals of a desired test procedure.

By way of example, the formation simulation material 32, e.g. sand pack, may be enclosed in a container or containers 28 formed of a metal material, such as stainless steel. In a specific example, the containers 28 comprise stainless steel cylinders having an internal diameter of approximately 2-3 cm, e.g. 2.54 cm, an external diameter of approximately 6-7 cm, e.g. 6.58 cm, and an effective inner length of 16-17 cm, e.g. 16.51 cm. However, a wide variety of other diameters and lengths may be employed depending on the desired test procedures and the overall design of system 20.

During a procedural example, the containers 28 are filled with sand, and the sand is retained within the containers 28, e.g. cylinders, by filter discs 88 placed generally at the entrance and exits of each container 28. By way of specific example, the filter disc 88 on the injection side may be 3.3 mm thick with pores ranging between 0.1 and 0.01 mm in diameter. These measurements may be used for each filter disc 88 and are one of several examples. A wide variety of other filter thicknesses and pore sizes may be used depending on the parameters of a given testing application. Each container 28, e.g. cylinder, may be sealed at its ends with appropriate end caps containing seals, such as O-rings. The distribution channels at the port through which fluid enters each container 28 may be designed to ensure that the entire cross-section of the filter disc 88 is involved in the flow and that the formation simulation material 32 is properly swept along the entire length of the core 30.

The containers 28 are placed in controlled heating baths 42. For example, containers 28 may be placed in controlled heating air baths, and the air temperature may be controlled while the air is circulated by a turbine or other suitable airflow source. The temperature of the injection and production lines, e.g. flow lines 52, 56, 58, 62, 72 and/or 76, may be monitored independently of the bath temperature with calibrated temperature sensors, e.g. thermocouples, such as temperature sensors 70.

In the embodiment illustrated, the core 30 of formation simulation material 32 has a plurality of pressure taps/ports 74 to report foam behavior in portions of the core 30. By way of example, the system may utilize three pressure taps 74 along each core 30 to report foam behavior in four portions of the core 30. However, other numbers of pressure taps 74 and pressure sensors 68 may be employed to monitor foam behavior and pressure differentials at other numbers of portions of the core 30. The pressure taps/ports 74 may be screened with appropriate filter discs having, for example, 0.05-0.15 mm (e.g. 0.1 mm) pore diameters, to retain the sand or other formation simulation material 32 in the container 28 upon pressurization. Filter discs also can be used to prevent material 32 from entering the fluid lines 72 coupled with the pressure sensors 68.

Figure 6:
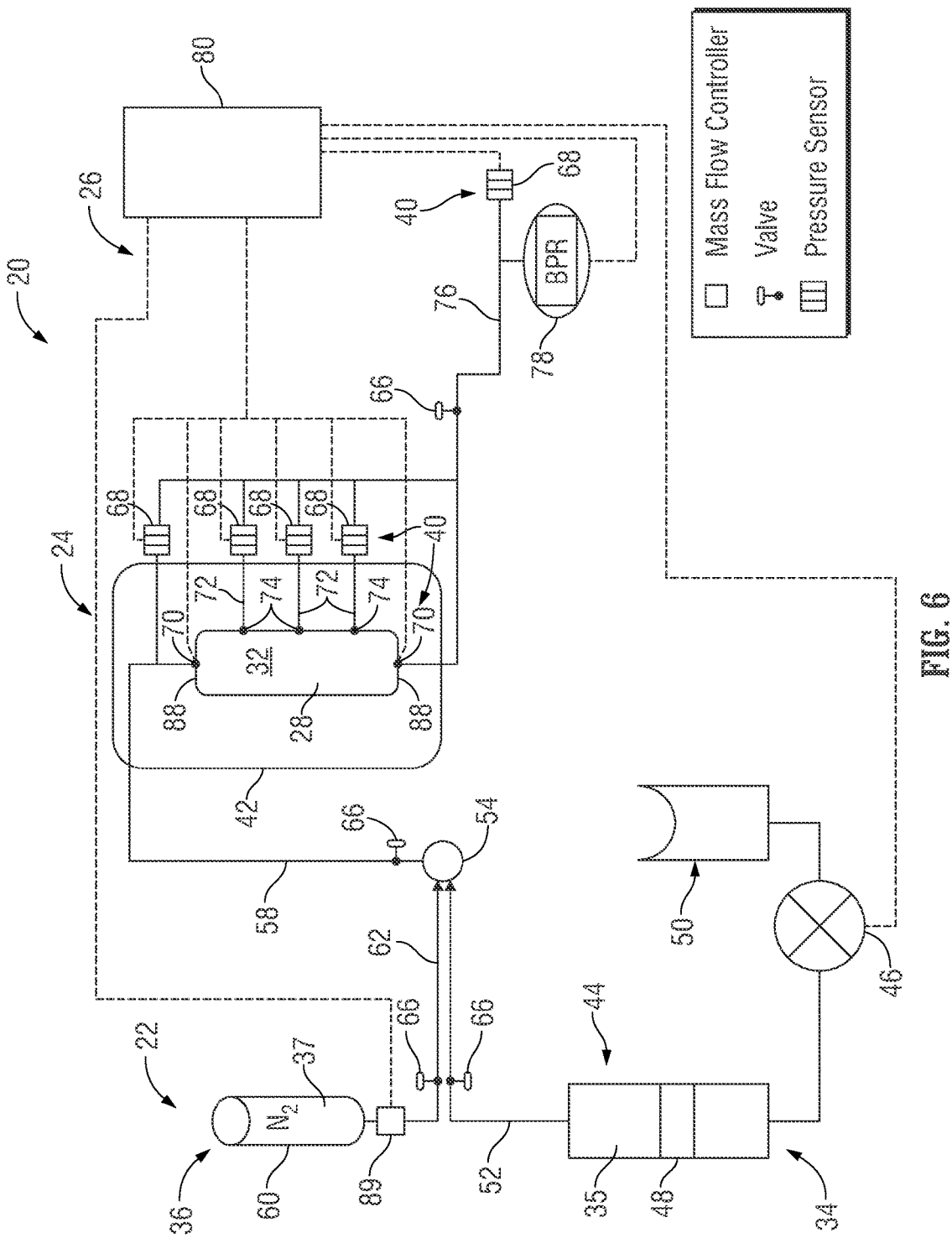
FIG. 6 is a schematic illustration of a more detailed example of a system for determining properties of a sample substance, when the methodology of FIG. 4 is utilized, according to an embodiment of the disclosure.

By way of further example presented in FIG. 6, the injection system 22 may comprise sample bottles 48 and 60 (liquid and gas) along with high pressure pump 46 and mass flow controller 89. In some applications, the injection fluid 37 is a gas in the form of a non-condensable nitrogen gas and gas injection bottle 60 is a high pressure bottle, e.g. a bottle pressurized at 6000 psi (421.8 kg/square cm) or more. Injection of the gas 37 may be controlled by mass flow controller 89. The liquid sample injection may be conducted at a desired flow rate by pump 46. Consequently, a desired gas/liquid ratio can be established during injection. The system 20 presented in FIG. 6 is well suited for conducting investigations according to the methodology of FIG. 4. Also, the injected fluids may be preheated to experimental temperatures within the fluid lines prior to entering the formation simulation material 32.

As described above, data acquisition system 26 may comprise differential pressure sensors 68 and temperature sensors 70. The data acquisition system 26 also may be designed as a control system for exercising control over, for example, mass flow controller 89 and pump 46. In some embodiments, the temperature of the core 30 is measured independently of the heating bath temperature using temperature sensors 70 in the form of, for example, J-type thermocouples located at the injection and production ends of the core 30, e.g. sand pack. The temperature sensors 70 may be selected to read within plus or minus 0.1° C. Additionally, the system may be designed so deviation between the targeted and actual temperature of the fluid is less than a predetermined amount, e.g. less than 2° C., during the actual experimentation process.

The differential pressure change along the core 30 during foam propagation of the sample substance 35 is measured at the pressure taps/ports 74. The pressure taps/ports 74 are ultimately connected to the flow line 76 which, in turn, is coupled with back pressure regulator 78 which provides the pressure reference point of the overall system. The flow lines 72 may be coupled through pressure sensors 68 which, in some embodiments, may be in the form of "Validyne" digitally compensated differential pressure transmitters, e.g. Model P855D, available from Validyne Engineering Corporation of Northridge, Calif., USA.

In some embodiments, pressure sensors 68 comprise differential pressure transmitters ranged from 0-1250 psi (0-87.9 kg/square cm) and positioned to effectively monitor foam propagation through the formation simulation material 32 of each core 30. The pressure sensors 68 also may comprise at least one additional sensor in the form of a differential pressure transducer ranged between, for example, 0-3200 psi (0-225 kg/square cm). The additional differential pressure transducer(s) may be employed to report the pressure difference between the pressure reference point of the system and the atmosphere to monitor changes in the back pressure regulator 78 pressure during the experiment. In some applications, the differential pressure transducers may have built-in thermal compensation to correct automatically for the minor fluctuations of ambient temperature during the measurements. Also, the pressure transducers may be installed in such a way that during the measurements malfunctioning individual pressure transducers can be replaced or corrected without interrupting the ongoing operation.

The data acquisition system 26 may comprise a variety of acquisition, analysis, and/or control systems. In some embodiments, the mass flow controller 89 and the pump 46 are controlled independently by data acquisition system 26. For example, processor or processors 38 (FIG. 3) may be part of personal computers used to monitor and control the mass flow controller 89 and pump 46 so as to continuously deliver fluids to cores 30 at a desired flow rate. The other sensors 40, e.g. pressure and temperature sensors, also may be connected to processor 38 of data processing unit 80, e.g. a personal computer or personal computers. In some applications, separate computers may be used for acquiring the data and for controlling various system components, such as the mass flow controller 89 and the pump 46.

A variety of software and programming may be utilized with data processing unit 80. For example, software may be designed to collect data, to enable a user to choose the data logging intervals, and to independently display various differential pressures and/or other data. The data processing unit also may be designed and programmed to plot in real-time the differential pressures measured by the selected pressure sensor 68 as a function of time. In some applications, software also may be selected to allow the user to switch between desired sensor readings, including temperature sensor readings. Additionally, the log data may be saved into memory 82 in a variety of forms, e.g. saved into an Excel® file. The differential pressure of any section of the core 30 can be calculated by taking a difference between the readings of the respective pressure sensors 68 along a given container 28. The storage file may be used to contain data from the various pressure and temperature sensors, including the pressure sensor used to monitor the back pressure regulator and the weight of the produced fluid from the mass balance. System 20 for can be run continuously for relatively long periods of time, e.g. days, without interruption.

Figure 4:
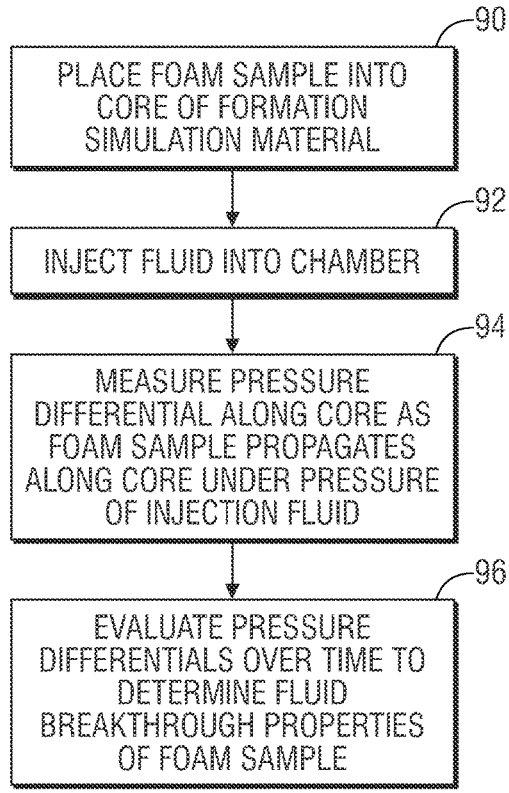
FIG. 4 is a flowchart illustrating an example of a methodology for determining properties of a sample substance, according to an embodiment of the disclosure.

Referring generally to FIG. 4, a flowchart is provided to illustrate an example of a methodology for determining gas breakthrough properties of a foam substance under constant injection rate conditions. In this example, a foam sample 35 is initially placed into a core 30 of formation simulation material 32, as indicated by block 90. Subsequently, an injection fluid 37 is injected into chamber 29 containing the formation simulation material 32, as indicated by block 92. Pressure differentials are measured along the core 30 of formation simulation material 32 as the foam sample 35 propagates along the core 30 under the pressure of the injection fluid 37, as indicated by block 94. The pressure differentials may be evaluated over time to determine fluid breakthrough properties of the foam sample 35, as indicated by block 96. The fluid breakthrough properties provide indications of the usefulness of the foam substance in delaying gas breakthrough during enhanced oil recovery processes.

Figure 5:
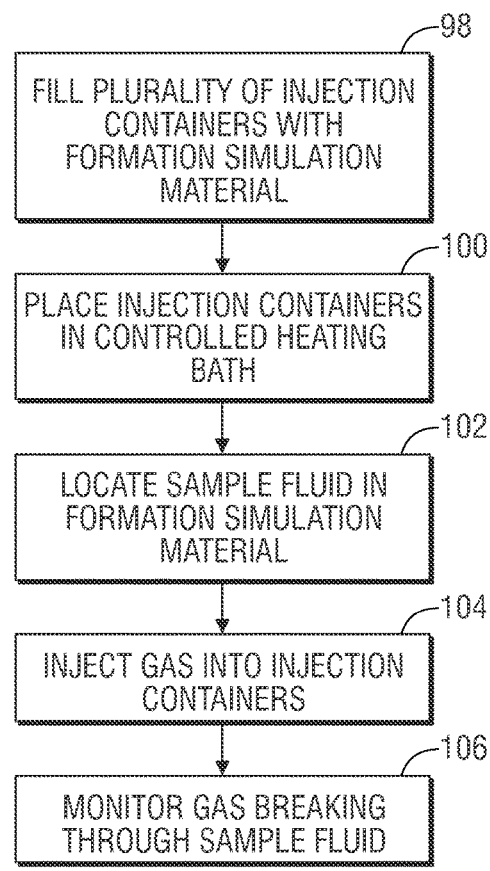
FIG. 5 is a flowchart illustrating another example of a methodology for determining properties of a sample substance, according to an embodiment of the disclosure.

Another example of a methodology for determining gas breakthrough is illustrated by the flowchart of FIG. 5 for constant differential pressure conditions. In this example, a plurality of injection containers 28 is filled with formation simulation material 32, as indicated by block 98. The injection containers 28 are placed in a controlled heating bath 42, as indicated by block 100. The controlled heating bath 42 is used to raise the temperature of the formation simulation material 32 to a desired temperature, such as a downhole well temperature. A sample fluid 35 is located in the formation simulation material 32, as indicated by block 102. Subsequently, a gas 37, e.g. nitrogen, is then injected into the injection containers 28, as indicated by block 104. Sensors 40 are then used to monitor propagation of the sample fluid 35 and gas breaking through the sample fluid 35, as indicated by block 106. Again, the gas breakthrough analysis can be used in determining the suitability of the sample substance for use in enhanced oil recovery processes and other types of processes.

The specific arrangement of system components for a given testing procedure may vary. For example, a variety of sensor types and sensor numbers may be deployed in combination with many types, shapes, and sizes of containers. Many types of formation simulation material may be used to represent various types of formations, including heterogeneous formations. Additionally, individual injection containers, pairs of injection containers, and greater numbers of injection containers may be used in a variety of testing systems. The various pumps, mass flow meters, back pressure regulators, and other system components may have a variety of sizes, shapes, capacities, and configurations depending on the parameters of a given testing system and on the samples to be tested. Similarly, various types of data acquisition and control systems may be used to accumulate and process data according to a number of programs, models, algorithms, and/or other types of software employed to determine and analyze parameters of a given sample substance.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method for determining foam properties, comprising:
    placing a foam sample into a container comprising a chamber packed with a core of a formation simulation material;
    injecting an injection fluid into the chamber;
    measuring pressure differentials along the core as the foam sample propagates along the core under a pressure of the injection fluid; and
    evaluating the pressure differentials over time to determine fluid breakthrough properties of the foam sample.

2. The method as recited in claim 1, further comprising constructing the container of stainless steel, and wherein the formation simulation material is in the form of sand.

3. The method as recited in claim 1, wherein the container is in the form of an injection cylinder.

4. The method as recited in claim 1, further comprising heating the container in a controlled heating bath.

5. The method as recited in claim 4, wherein the controlled heating bath is a controlled heating air bath.

6. The method as recited in claim 1, further comprising placing filters along the formation simulation material at an entry and an exit of the chamber.

7. The method as recited in claim 1, wherein placing the foam sample into a container comprises placing the foam sample into a plurality of containers, each container having a chamber.

8. The method as recited in claim 7, wherein each container is in the form of an injection cylinder.

9. The method as recited in claim 8, further comprising orienting the injection cylinders in a vertical position.

10. A system for determining properties of a sample substance, comprising:
    a container filled with a formation simulation material;
    an injection system coupled to the container, the injection system comprising a sample injector, positioned to inject a sample into the formation simulation material, and a gas injector coupled to the container to inject a gas into the container after the sample permeates into the formation simulation material to cause foam propagation of the sample;
    a data acquisition system coupled to the container and comprising a processor in communication with a plurality of pressure sensors deployed along the container, the pressure sensors providing data to the processor for determination of pressure differentials along the formation simulation material located within the container.

11. The system as recited in claim 10, wherein the container comprises a plurality of containers.

12. The system as recited in claim 11, wherein the gas injector comprises a high pressure bottle containing nitrogen.

13. The system as recited in claim 12, wherein the data acquisition system comprises a back pressure regulator coupled to a plurality of pressure taps along the container.

* * * * *